United States Patent [19]

Masuda et al.

[11] 4,435,681
[45] Mar. 6, 1984

[54] BIPOLAR IONIC CURRENT PROBE UNIT AND METHOD FOR MEASURING POSITIVE AND NEGATIVE CURRENT DENSITIES BY MEANS OF THE SAME PROBE UNIT

[76] Inventors: Senichi Masuda, No. 605, Nishigahara 1-40-10, Kita-ku, Tokyo-to; Yutaka Nonogaki, 2-61-1-702, Denenchofu, Ohta-ku, Tokyo-to, both of Japan

[21] Appl. No.: 306,515

[22] Filed: Sep. 28, 1981

[51] Int. Cl.³ ............................................. G01N 27/62
[52] U.S. Cl. ..................................... 324/459; 324/464; 324/466; 324/72; 324/71.1
[58] Field of Search ....................... 324/459, 464, 71.1, 324/71.4, 72.5, 466, 72

[56] References Cited
FOREIGN PATENT DOCUMENTS
1003043  4/1977  Canada .................................. 324/466

Primary Examiner—Michael J. Tokar
Assistant Examiner—Kevin D. O'Shea
Attorney, Agent, or Firm—Price, Heneveld, Huizenga & Cooper

[57] ABSTRACT

A tri-electrode probe consisting of a central electrode and a pair of measuring electrodes on the opposite sides of the central electrode disposed so as to symmetrically cover an immaginary surface having a plane of symmetry, is connected to a measuring system including minute current ammeters and a variable D.C. voltage source, the tri-electrode probe is positioned at a measuring point within an electric field where both positive and negative ions coexist as oriented in such direction that the plane of symmetry is directed in perpendicular to the direction of the electric field with one of the measuring electrodes opposed to a negative ion source and the other measuring electrode opposed to a positive ion source, a current flowing through the minute current ammeter connected to the central electrode is made substantially zero by varying the voltage of the variable D.C. voltage source, at that moment the current values indicated by the minute current ammeters connected to the measuring electrodes are read out, and positive and negative ionic current densities in the electric field are determined on the basis of the read current values.

4 Claims, 10 Drawing Figures

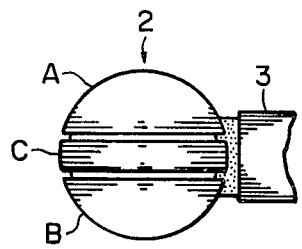
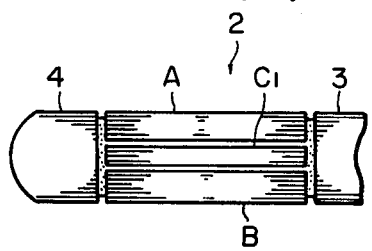
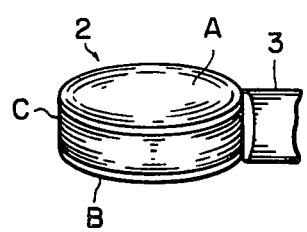
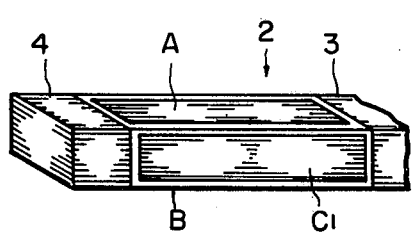
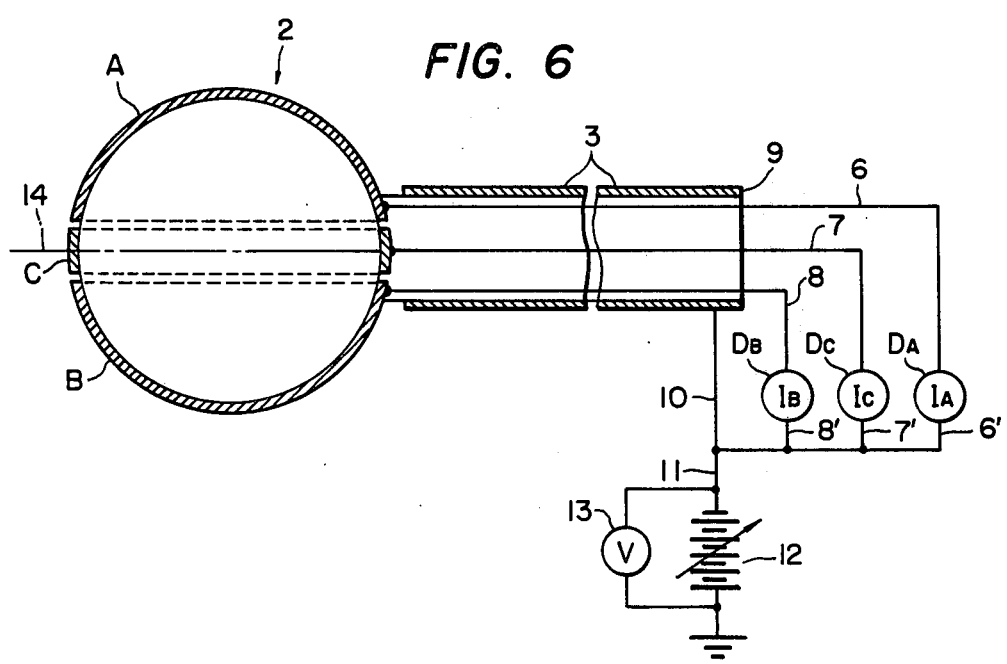

BIPOLAR IONIC CURRENT PROBE UNIT AND METHOD FOR MEASURING POSITIVE AND NEGATIVE CURRENT DENSITIES BY MEANS OF THE SAME PROBE UNIT

BACKGROUND OF THE INVENTION

The present invention relates to a bipolar ionic current probe unit adapted to measure a positive ionic current density and a negative ionic current density and a method for measuring positive and negative ionic current densities by means of the same bipolar ionic current probe unit.

Heretofore, in an electric dust-collecting apparatus for collecting dust having an extremely high electric resistance, after a voltage drop across a dust layer accumulated on a dust-collecting electrode would become excessively large, resulting in dielectric breakdown, and thus the so-called back ionization would occur, which causes abnormal positive corona discharge from the dust-collecting electrode towards a discharge electrode of negative polarity. This served as a principal factor for greatly degrading the dust-collecting performance of the apparatus. This degradation of the dust-collecting performance is caused by the fact that negative charge on the dust which was applied by bombardment by a negative ionic current produced by negative corona discharge of the discharge electrode is neutralized and reduced by a positive ion current fed by the above-mentioned anomalous positive corona discharge and consequently a Coulomb's force necessitated for collecting dust is greatly weakened. In this instance, even when the ratio $\beta = i_+/i_-$ of a positive ionic current density $i_+$ to a negative ionic current density $i_-$ is as small as only 10%, a quantity of electric charge Q on the dust is reduced to 50% with respect to its ideal value $Q_o$ which can be attained by negative ions fed from the discharge electrode upon normal operation when no back ionization occurs, and as the value of the ratio $\beta$ is increased successively to 20%, 30% and 40%, the quantity of electric charge Q is widely reduced to 30%, 20% and 10%, respectively, of the ideal value $Q_o$, so that remarkable degradation of the dust-collecting performance is resulted to the corresponding extent. In order to investigate such anomalous phenomena, to confirm the extent of degradation and to appropriately control voltages, currents and the like in a dust-collecting apparatus on the basis of the results of investigation and confirmation, it is necessary to measure a positive ionic current density $i_+$ and a negative ionic current density $i_-$ individually and separately within an electric field in which both positive and negative ionic currents coexist. However, in the prior art such separate measurement was considered to be impossible, and a big problem of achieving such separate measurement of positive and negative ionic current densities has been left unsolved up to the present.

SUMMARY OF THE INVENTION

It is therefore one object of the present invention to provide a novel bipolar ionic current probe unit which enables simultaneous and individual measurement of positive and negative ionic current densities within an electric field where both positive and negative ions coexist.

Another object of the present invention is to provide a novel method for simultaneously and individually measuring positive and negative ionic current densities by means of a newly designed probe unit.

According to one feature of the present invention there is provided a bipolar ionic current probe unit comprising a tri-electrode probe, which includes a narrow elongated central electrode insulatively disposed on an imaginary surface of a small shape having a plane of symmetry along a line of intersection between said imaginary surface and said plane of symmetry and a pair of measuring electrodes insulatively disposed on said impaginary surface portions on the opposite sides of said central electrode in a symmetric manner with respect to the line of intersection so as to cover substantially the entire imaginary surface portions on the opposite sides with a small fixed gap clearance spaced from said central electrode, a hollow metallic support post for insulatively supporting said tri-electrode probe, and a measuring system, which includes individual electrid conductors respectively connected to said central electrode and said measuring electrodes and extending through the hollow space in said hollow metallic support post as insulated from said hollow metallic support post and from each other, means for measuring minute electric currents with one end connected to said individual electric conductors and the other end connected through a common electric conductor to said hollow metallic support post, and a variable D.C. voltage source connected between said common electric conductor and a reference potential point.

According to another feature of the present invention, there is provided a method for simultaneously and individually measuring positive and negative ionic current densities within an electric field where both positive and negative ions coexist by means of a bipolar ionic current probe unit comprising a tri-electrode probe, which includes a narrow elongated central electrode insulatively disposed on an imaginary surface of a small shape having a plane of symmetry along a line of intersection between said imaginary surface and said plane of symmetry, and a pair of measuring electrodes insulatively disposed on said imaginary surface portions on the opposite sides of said central electrode in a symmetric manner with respect to said line of intersection so as to cover substantially the entire imaginary surface portions on the opposite side with a small fixed gap clearance spaced from said central electrode, a hollow metallic support post for insulatively supporting said tri-electrode probe, and a measuring system, which includes individual electric conductors respectively connected to said central electrode and said measuring electrodes and extending through the hollow space in said hollow metallic support post as insulated from said hollow metallic support post and from each other, means for measuring minute electric currents with one end connected to said individual electric conductors and the other end connected through a common electric conductor to said hollow metallic support post, and a variable D.C. voltage source connected between said common electric conductor and a reference potential point; consisting of the steps of positioning said tri-electrode probe at a measuring point within said electric field as oriented in such direction that said plane of symmetry is directed in perpendicular to the direction of said electric field with one of said measuring electrodes opposed to a source of negative ions and the other measuring electrode opposed to a source of positive ions, varying the voltage of said variable D.C. voltage source to change the potentials of the central electrode and the measuring electrodes in said tri-electrode probe as well as said hollow metallic support powt until said minute electric current measuring means detects substantially zero current flowing through the individual electric conductor connected to said central electrode, then measuring the minute electric currents flowing through the individual electric conductors connected to said respective measuring electrodes, and deriving the positive and negative ionic current densities, respectively, on the basis of the measured values of said minute electric currents flowing through the individual electric conductors connected to said respective measuring electrodes.

In practicing the above-featured bipolar ionic current probe unit, the central electrode and the pair of measuring electrodes could be respectively supported by an appropriate insulator body so as to hold predetermined configurations and arrangement as insulated from each other. In one mode of embodiment, an insulator body having an outer surface conformed to the imaginary surface can be used for supporting the central and measuring electrodes. Alternatively, the central and measuring electrodes can be deposited on the insulator support body having an outer surface conformed to the imaginary surface through a process of vapor deposition, plating, thick film technique, application of conductive paint, or the like. The minute current measuring means can be formed of three individual minute current anmeters having their one terminals connected respectively to the individual electric conductors and the other terminals connected in common to the common electric conductor. However, in an alternative embodiment, the minute current measuring means can be formed of a single minute current anmeter and a transfer switch for selectively connecting one terminal of the minute current anmeter to one of the individual electric conductors, with the other terminal of the minute current anmeter connected permanently to the conmon electric conductor.

In practicing the above-featured method for measuring positive and negative current densities, determination of the equilibrium condition where substantially zero current flows through the individual electric conductor connected to the central electrode can be achieved by manually varying the voltage of the variable D.C. voltage source while watching indication of the minute electric current measuring means. However, in an alternative embodiment, an output signal from the minute electric current measuring means indicating the value of the current flowing through the individual electric conductor connected to the central electrode, could be electrically fed back to the veriable D.C. voltage source in the polarity for reducing the output signal so that the variable D.C. voltage source may be automatically controlled to realize substantially zero current flowing through the individual electric conductor connected to the central electrode. Furthermore, in place of realizing the condition where substantially zero current flows through the individual electric conductor connected to the central electrode and measuring the minute electric currents flowing through the individual electric conductors connected to the respective measuring electrode under that condition, the relations between the voltage of the variable D.C. voltage source and the minute currents flowing through the respective individual electric conductors could be preliminarily measured and plotted either manually or automatically. Then the desired measured values of the minute electric currents flowing through the individual electric conductors connected to the respective measuring electrodes can be obtained from the plotted voltage-current curves through the process as will be fully described later.

BRIEF DESCRIPTION OF THE DRAWINGS

In the accompanying drawings:

FIG. 4 is an external view showing various configurations of a tri-electrode probe forming the principal structure of the bipolar ionic current probe unit according to the present invention, FIG. 6 is a longitudinal cross-section view showing a principal structure of another preferred embodiment of a novel bipolar ionic current probe unit according to the present invention associated with a schematic circuit diagram of a measuring system in the probe unit.

DESCRIPTION OF PREFERRED EMBODIMENT

Figure 1:
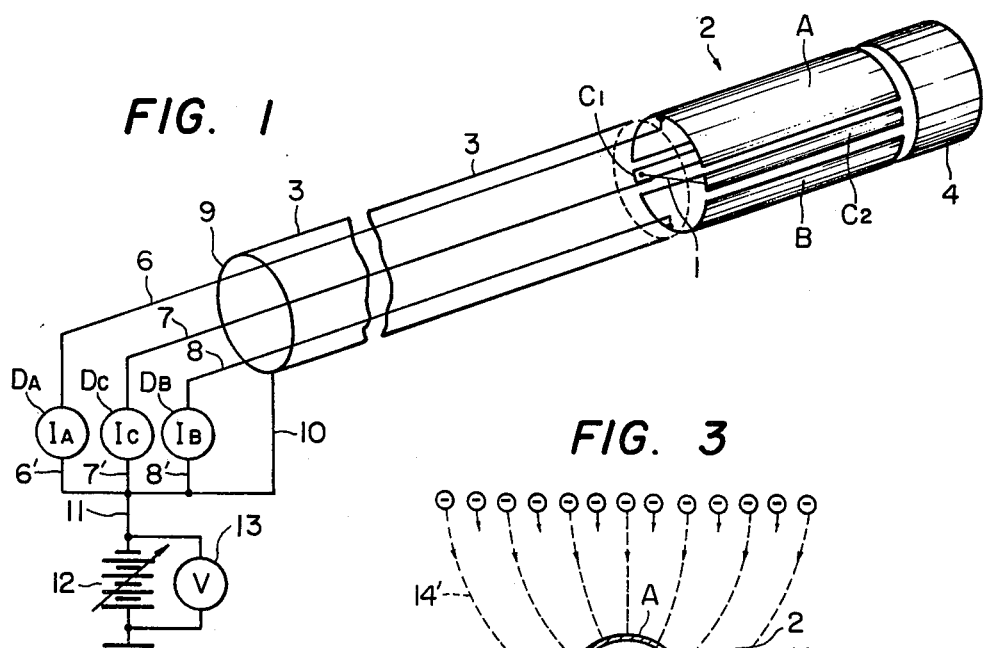
FIG. 1 is a perspective view showing a principal structure of one preferred embodiment of a novel bipolar ionic current probe unit according to the present invention associated with a schematic circuit diagram of a measuring system in the probe unit.

At first, a principle of the present invention will be described in detail in connection to a first preferred embodiment of a bipolar ionic current probe unit according to the present invention illustrated in FIGS. 1, 2, 3 and 4(b), in which a cylindrical surface is employed as an imaginary surface. Naturally, the illustrated imaginary cylindrical surface is symmetrical with respect to a plane including its center axis, and a line of intersection S between the imaginary surface and the plane of symmetry consists of two straight lines lying on the cylindrical surface symmetrically with respect to its center axis. Along there straight lines, narrow elongated rectangular electrodes $C_1$ and $C_2$ are disposed on the cylindrical surface with the straight lines positioned on the center lines of the electrodes, and they are connected to each other through a lead wire 1 to form one central electrode C. It is to be noted that in these figures, for the purpose of clarification of illustration, an insulator body for insulatively supporting the respective electrodes are omitted from illustration. On the opposite sides of the electrodes $C_1$ and $C_2$ are insulatively disposed two semi-cylindrical measuring electrodes A and B on the cylindrical imaginary surface with a small gap clearance spaced from these electrodes $C_1$ and $C_2$, and these measuring electrodes A and B as well as the central electrode C jointly form a cylindrical tri-electrode probe 2. Reference numeral 3 designates a hollow metallic support post having the same outer diameter as the probe 2 and disposed coaxially therewith, which support post is, in the illustrated embodiment, of cylindrical shape. This support post 3 supports the tri-electrode probe 2 via an insulator body or bodies not shown. Reference numeral 4 designates a guard electrode consisting of a metallic cup having the same outer diameter as the tri-electrode probe 2, which guard electrode is disposed insulatively and coaxially with the probe 2 for the purpose of preventing an electric field from concentrating to the other end of the tri-electrode probe 2.

The central electrode $C_1$-$C_2$ and the measuring electrodes A and B are connected to three lead wires 7, 6 and 8 extending through the hollow space in the hollow metallic support post 3. These lead wires are derived externally from a base outlet port 9 of the hollow metallic support post 3 and connected respectively to one terminals of minute current ammeters $D_A$, $D_C$ and $D_B$, respectively. The other terminals of the ammeters $D_A$, $D_C$ and $D_B$ are connected to lead wires 6', 7' and 8', respectively, and these lead wires 6', 7' and 8' as well as another lead wire 10 connected to the hollow metallic support post 3 are connected via a common lead wire 11, in the illustrated example, to a negative terminal of a variable D.C. high voltage source 12 whose positive terminal is grounded. Reference numeral 13 is a voltmeter for indicating a terminal voltage of the voltage source 12.

Figure 3:
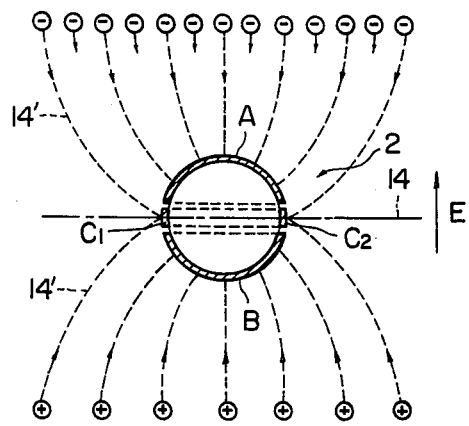
FIG. 3 is a transverse cross-section view of the principal structure of the probe unit shown in FIG. 1.
Figure 2:
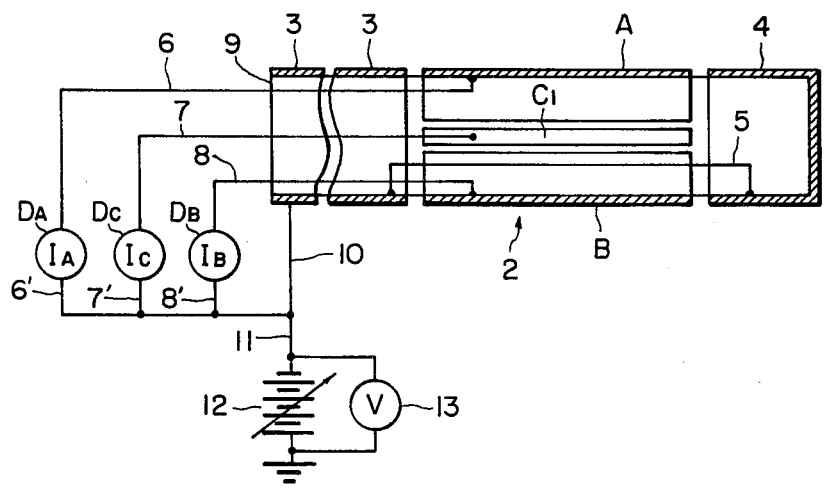
FIG. 2 is a longitudinal cross-section view of the principal structure associated with the schematic circuit diagram of the probe unit shown in FIG. 1.

Upon measurement, the tri-electrode probe 2 is positioned by the intermediary of the hollow metallic support post 3 at a measuring point within an electric field E where both positive and negative ionic currents coexist, and as shown in FIG. 3, the tri-electrode probe 2 is supported as oriented in such direction that a plane of symmetry 14 including center lines of the central electrode $C_1$-$C_2$ of the probe 2 is directed in perpendicular to the direction of the electric field E with one measuring electrode A opposed to a negative ion source and the other measuring electrode B opposed to the other electrode B. Then the voltage V of the variable D.C. high voltage source 12 is varied so as to equalize the potential of the tri-electrode probe 2 to the original potential before insertion of the probe 2 at the measuring point. This condition is called "equilibrium condition" and the potential of the probe 2 at this moment is called "equilibrium potential".

At this moment, lines of electric force 14' becomes perfectly symmetrical with respect to the plane of symmetry 14, in the spaces above and below the plane of symmetry 14 as viewed in FIG. 3. It is to be noted that in the illustrated example, the direction of the lines of electric force 14' is such that they enter into the electrode B from the below and emanate from the electrode A to the above. In the illustrated case, the number of lines of electric force entering into the electrode B would exactly coincide with the number of lines of electric force emanating from the electrode A. In addition, at the electrode $C_1$ or $C_2$, since the number of lines of electric field entering into the electrode and the number of lines of electric force emanating from the same electrode are equal to each other, the net number of lines of lines of electric entering into or emanating from the electrode is zero.

Positive ions flow into the electrode B from the below along the lines of electric force, and the total positive ionic current $I_+$ is indicated by the ammeter $D_B$ as a positive current $I_B = I_+$. Whereas, negative ions flow into the electrode A from the above along the lines of electric force, and the total negative ionic current $I_-$ is indicated by the ammeter $D_A$ as a negative current $I_A = I_-$. The positive and negative ionic currents $I_B = I_{+o}$ and $I_A = I_{-o}$ flowing into the electrodes B and A, respectively, under the equilibrium condition are called "equilibrium ionic current". When a positive ionic current density $i_+$ and a negative ionic current density $i_-$ are different from each other, a current $I_{CO}$ flows into the central electrode $C_1$-$C_2$ under equilibrium condition although the current has a small value, and the current $I_{CO}$ becomes positive when the relation of $i_+ > i_-$ is fulfilled, and becomes negative when the condition $i_+ < i_-$ is fulfilled. However, in either case, if the width of the central electrode $C_1$-$C_2$ is selected to be sufficiently small, then the current $I_{CO}$ takes an extremely small value. Under the equilibrium condition, theoretically the following relations are established between the positive and negative ionic current densities $i_+$ and $i_-$ [A/m²] and the positive and negative equilibrium ionic currents $I_{+o}$ and $I_{-o}$ [A], respectively, detected at the measuring electrode B and the measuring electrode A:

$$I_{+o} = 4al \cos(d/2a) i_+ \ [A] \quad (1)$$

$$I_{-o} = 4al \cos(d/2a) i_- \ [A] \quad (2)$$

where a represents a radius of the cylindrical imaginary surface in meters, d represents a width of the central electrodes $C_1$ and $C_2$ in meters, and l represents a axial length of the electrodes A, B, $C_1$ and $C_2$ in meters.

In other words, the equilibrium ionic currents $I_{+o}$ and $I_{-o}$ are respectively proportional to the positive and negative ionic current densities $i_+$ and $i_-$, and therefore, the ionic current densities $i_+$ and $i_-$ can be directly derived from the measured values of the equilibrium ionic currents $I_{+o}$ and $I_{-o}$, respectively. With regard to the methods for establishing the equilibrium condition, the following methods are conceived.

Figure 5:
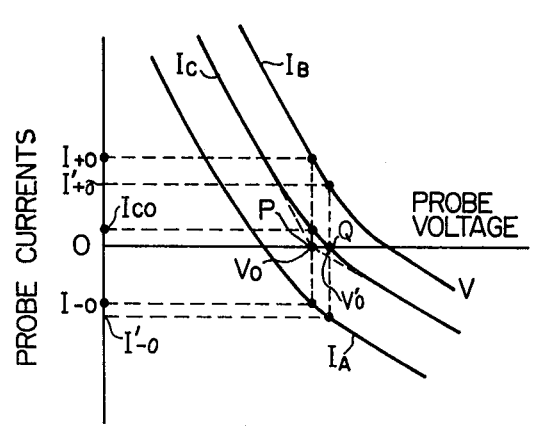
FIG. 5 is a characteristic diagram showing the relation of a probe voltage versus probe currents of the bipolar ionic current probe unit according to the present invention.

A first method is a method of extrapolation. That is, when the currents $I_C$, $I_A = I_-$ and $I_B = I_+$ flowing from the respective electrodes C, A and B, respectively, to the ammeters $D_C$, $D_A$ and $D_B$ are measured while varying the voltage V of the variable D.C. high voltage source 12, current-voltage characteristic curves $I_C$, $I_A$ and $I_B$ as shown in FIG. 5 can be obtained. Every one of these curves consists of two straight line sections and a curved section therebetween. Then a point of intersection P between the extrapolated extensions of the straight line sections of the curve $I_C$ and the abscissa gives the above-referred equilibrium potential $V_o$, and as shown in FIG. 5, the current values $I_B$ and $I_A$ for the voltage $V = V_o$ afford the exact equilibrium ionic currents $I_{+o}$ and $I_{-o}$ to be substituted in the Equations (1) and (2) above. At this moment (for the voltage $V_o$), as shown in FIG. 5 a small equilibrium ionic current $I_{CO}$ is flowing through the central electrode $C_1$-$C_2$. Determination of the equilibrium ionic currents $I_{+o}$ and $I_{-o}$ relying upon extrapolation as described above, can be executed quickly and automatically by means of a preliminarily programmed electronic computer.

Another method for establishing the equilibrium condition is a method of quasi-equilibrium. More particularly, the equilibrium potential $V_o$ is approximated by a potential $V_o'$ (at point Q) for which the current $I_C$ flowing through the central electrode C becomes zero. This is called "quasi-equilibrium potential". The values $I_{+o}'$ and $I_{-o}'$ of the currents $I_B$ and $I_A$, respectively, at this point Q are called "quasi-equilibrium ionic currents", and they are substituted into the Equations (1) and (2) above as approximate values of the true equilibrium ionic currents $I_{+o}$ and $I_{-o}$ to derive the positive and negative ionic current densities $i_+$ and $i_-$. In this method, although the precision becomes higher as the width of the central electrode C is narrowed, on the other hand the sensitivity for detection of the condition of $I_C=0$ is lowered according to the narrowing of the central electrode C. Accordingly, as one solution for this problem, another method can be employed, in which the width of the electrode C is selected to a centain extent large, and by multiplying the measured values of the positive and negative quasi-equilibrium ionic currents $I_{+o}'$ and $I_{-o}'$ flowing through the measuring electrodes B and A, respectively, under the condition of $I_C=0$ by theoretically determinable correction factors $k_+$ and $k_-$ (theoretically determined as functions of the ratio of $I_B$ to $I_A$), the correct positive and negative equilibrium ionic currents $I_{+o}=k_+\cdot I_{+o}'$ and $I_-=k_-\cdot I_{-o}'$ are determined. Moreover, including this correction operation, the determination of the equilibrium ionic currents $I_{+o}$ and $I_{-o}$ according to the method of quasi-equilibrium can be quickly executed by making use of a preliminarily programmed electronic computer.

FIG. 6 shows another preferred embodiment of the present invention in which a spherical surface is employed as the above-described imaginary surface, and this figure shows a spherical type bipolar ionic current probe in longitudinal cross-section. A side view of the same tri-electrode probe of spherical type is shown in FIG. 4(a). In these figures, reference numeral 2 designates a tri-electrode probe, in which a line of intersection S between the spherical imaginary surface and one of the planes of symmetry thereof 14 forms an equator curve, a narrow annular central electrode C is insulatively disposed along this line of intersection S with the center line of the central electrode C placed thereon, and on the imaginary surface portions on the opposite sides of the central electrode C are insulatively disposed mutually symmetric hemi-spherical measuring electrodes A and B with a small fixed gap clearance spaced from the central electrode C. In FIGS. 4(a) and 6, the names and functions of the component parts denoted by reference numerals 3 to 13 are identical to the component parts denoted by like reference numerals in FIGS. 1, 2, 3 and 4(b). The principle and operation of the second preferred embodiment have no difference from those of the cylindrical type bipolar ionic current probe unit described previously with reference to FIGS. 1, 2, 3, 4(b) and 5, and hence they are self-explanatory from the preceding explanation of the first preferred embodiment. Therefore, further description of the second preferred embodiment will be omitted. However, it is to be noted that in the spherical type bipolar ionic current probe unit, the guard electrode 4 is not provided because it is unnecessary, and the following theoretical relations are established between the positive and negative equilibrium ionic currents $I_B=I_{+o}[A]$ and $I_A=I_-[A]$ detected at the respective measuring electrodes B and A when the potential V of the probe is brought to the equilibrium potential $V_o$ and the positive and negative ionic current densities $i_+[A/m^2]$ and $i_-[A;m^2]$:

$$I_{+o}=3\pi a^2 \cos^2(d/2a)i_+[A] \quad (3)$$

$$I_{-o}=3\pi a^2 \cos^2 9d/2a)i_-[A] \quad (4)$$

where a represents a radius of the spherical imaginary surface in meters, d represents a width of the central electrode C in meters. Therefore, the ionic current densities $i_+$ and $i_-$ can be directly derived from the measured values of the equilibrium ionic currents $I_{+o}$ and $I_{-o}$, respectively. With regard to the methods for establishing the equilibrium condition, they are exactly the same as those discussed previously in the case of the cylindrical type bipolar ionic current probe unit.

The above-described spherical type bipolar ionic current probe unit is suitable for precisely measuring the positive and negative ionic current densities $i_+$ and $i_-$ at one given point within a three-dimensional electric field because the tri-electrode probe 2 is formed in a spherical shape. On the other hand, however, in this modified embodiment there exists an influence of disturbances in an electric field and ionic currents caused by the hollow metallic support post 3, and therefore it is necessary to make the hollow metallic support post 3 as thin as possible.

FIG. 4 shows various examples of the configuration of the tri-electrode probe 2. In the probe 2 shown in FIG. 4(c), a flat cylindrical surface is employed as an imaginary surface, a central electrode C is formed of an annular electrode disposed along its narrow side surface, and measuring electrodes A and B are formed of circular electrodes disposed on its top and bottom circular planes and having a somewhat smaller diameter than that of the circular planes. In the probe 2 shown in FIG. 4(d), a parallelopiped surface is employed as the imaginary surface, central electrodes $C_1$ and $C_2$ are formed of rectangular electrodes disposed along its opposite elongated side surfaces, and measuring electrodes A and B are formed of rectangular electrodes disposed on its top and bottom rectangular planes. In this configuration of probe 2, both the guard electrode 4 and the hollow metallic support post 3 are formed in a parallelopiped shape.

When the bipolar ionic current probe unit according to the present invention is employed, accurrence of back ionization as well as a degree of trouble caused by the back ionization can be detected in a very sensitive and precise manner. Therefore, automatic control for suppressing back ionization in various types of electric dust-collecting apparatuses can be achieved by making use of the bipolar ionic current probe unit according to the present invention.

Figure 7:
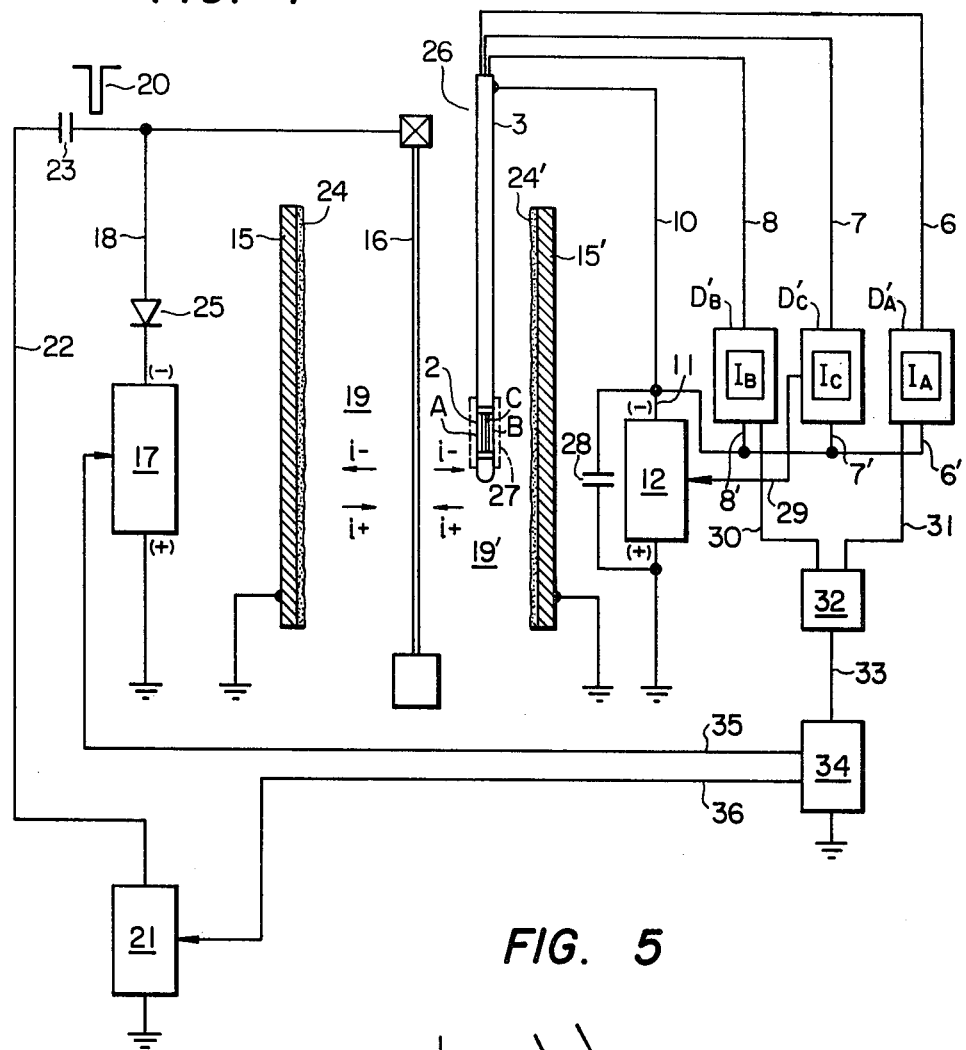
FIG. 7 is a system diagram of a pulse-charging type electric dust collector in which optimum control is achieved by making use of the novel bipolar ionic current probe unit according to the present invention as means for detecting back ionization.

FIG. 7 is a system diagram showing one example of such applications of the present invention, in which the novel cylindrical type bipolar ionic current probe unit according to the present invention is used as a detector section for performing optimum control in "a pulse-charging type electric dust-collecting apparatus" which is a subject matter of the prior invention invented by the inventor of this application (Japanese Patent Appln. No. 51-073004). In this figure, reference numerals 15 and 15' designate grounded dust-collecting electrodes, and reference numeral 16 designates a discharge electrode that is insulatively stretched at a midpoint between the electrodes 15 and 15', which discharge electrode is applied with a negative D.C. high voltage $V_{dc}$ that is little lower than a corona start voltage $V_C$, from a D.C. high voltage source 17 via a lead wire 18, to establish a main electric field E within dust-collecting spaces 19 and 19' between the dust-collecting electrodes 15, 15' and the discharge electrode 16. At the same time, a negative pulse voltage 20 having a pulse duration $\tau_P$, a wave crest $V_p$ a repetition frequency $f_p$ is applied as superposed on the D.C. high voltage $V_{dc}$ from a pulse voltage source 21 though a lead wire 22 and a coupling capacitor 23 to the discharge electrode 16. As a result, pulse corona discharge occurs at the discharge electrode 16 only upon application of the pulses, and hence a negative ionic current flows towards the dust-collecting electrodes 15 and 15'. Accordingly, dust particles entering into the dust-collecting spaces 19 and 19' are subjected to bombardment by these negative ions and charged negatively, hence they are subjected to Coulomb's forces under the action of the above-described main electric field E to be driven and removed towards the dust-collecting electrodes 15 and 15', and they are deposited and accumulated on these dust-collecting electrodes 15 and 15', resulting in formation of dust layers 24 and 24'. Reference numeral 25 designates a rectifier element for preventing the pulse voltage 20 from entering into the D.C. high voltage source 17. At this moment, if the electric resistance of the dust to be collected is high, then the dust layers 24 and 24' would behave as an insulative layer against the above-described negative ionic current, so that an extremely large voltage drop would arise across the dust layer 24 or 24', eventually dielectric breakdown occurs in the dust layers 24 and 24', hence positive corona is produced from the dust layers 24 and 24' towards the dust-collecting spaces 19 and 19', and thus back ionization phenomena occur. Consequently, a positive ionic current flows from these dust layers 24 and 24', and this positive ionic current would remarkably degrade the dust-collecting performance of the apparatus by neutralizing the negative charge on the dust particles which charge is necessary for collection of the dust particles. In order to operate the above-described pulse-charging type dust-collecting apparatus while perfectly preventing such back ionization phenomena, it is necessary to detect occurrence of back ionization and to operate the apparatus while fulfilling the following two control conditions:

(1) By controlling the pulse duration $\tau_P$, pulse crest value voltage $V_p$ and/or pulse repetition frequency $f_p$, the negative ionic current density $i_-$ is reduced so that an average value $\bar{i}_-$ of the negative ionic current density may fulfil the following relation for a given specific resistance $\rho_d$ of the dust layer:

$$\bar{i}_- \times \rho_d < E_{ds}, \quad (5)$$

where $E_{ds}$ represents a dielectric breakdown field strength in the dust layer, and thereby dielectric breakdown of the dust layer is prevented.

(2) The D.C. voltage $V_{dc}$ is controlled so that the main electric field strength E may be held equal to or lower than a fixed value $E_o$ adapted for always suppressing growth and propagation to a wide region of back ionization.

In FIG. 7, reference numeral 26 designates a novel bipolar ionic current probe unit according to the present invention as used for detecting back ionization in an electric dust-collecting apparatus for the above-mentioned purpose, and the probe unit 26 is inserted from the above into the dust-collecting space 19' between the discharge electrode 16 and the dust-collecting electrode 15' in parallel to these electrodes. It is to be noted that the tri-electrode probe 2 in the probe unit 18 is electrically shielded by a wire gauze 27 connected to the hollow metallic support post 3 to prevent the respective probe electrodes A, B and C from detecting an induction noise voltage caused by the pulse voltage 20, while the wire gauze 27 allows positive and negative ionic currents to pass therethrough. In addition, to the probe unit 26 is applied a negative D.C. voltage from a variable D.C. voltage source 12 through a lead wire 10, and a by-pass capacitor 28 is connected in parallel to the voltage source 12 to by-pass a noise voltage induced on the wire gauze 27 and the hollow metallic support port 3 by the pulse voltage 20 to the ground, so that the noise voltage may not substantially interfere with the results of measurement. In this case, for the purpose of making the prevention of a noise more perfect, it is preferable to employ a double shield system in which the hollow metallic support post 3 and the wire gauze 27 are formed in a double structure. Now it is assumed that the tri-electrode probe 2 at the tip end of the probe unit 26 has been positioned at a measuring point, and as described previously, the plane of symmetry including the central electrode C has been directed in perpendicular to the electric field. At this moment, the ionic current $I_c$ flowing into the probe 2 through the central electrodes $C_1$ and $C_2$ is detected and amplified by a current detection control device $D'_C$, and an output signal from the current detection control device $D_{C'}$ is fed back to a voltage regulator section in the variable D.C. voltage source 12, so that the output voltage V of the variable D.C. voltage source 12 can be automatically controlled to reduce the ionic current $I_C$ to zero, and thereby a quasi-equilibrium condition can be established. At this moment, the positive and negative quasi-equilibrium currents $I_B = I_{+o}'$ and $I_A = I_{-o}'$ flowing into the measuring electrodes B and A, respectively, are detected by minute current detection devices $D_B'$ and $D_A'$, the output signals from these devices are further transmitted through lead wires 30 and 31 to a signal processing and converting device 32, in which correction factors $k_+$ and $k_-$ corresponding to a given ratio of $I_{+o}'/I_{-o}'$ are calculated to derive the correct equilibrium ionic currents $I_{+o} = k_+ \cdot I_{+o}'$ and $I_{-o} = k_- \cdot I_{-o}'$, and further the positive and negative ionic current densities $i_+$ and $i_-$ are determined on the basis of these derived values of the equilibrium ionic currents. Then, for the purpose of transmitting the signals representing the positive and negative ionic current densities $i_+$ and $i_-$ from the signal processing and converting device 32 held at a high potential to a control section held at the ground potential, the electric signals representing the current densities $i_+$ and $i_-$ are converted into light signals, and these light signals are transmitted via an optical fiber 33 to a power supply control section 34. In the control section 34, the value of the positive ionic current density $i_+$ or the ratio of ionic current densities $i_+/i_-$ is used as a control parameter. Then, control signals are transmitted via lead wires 35 and 36 to the D.C. high voltage source 17 which applies a D.C. high voltage to the discharge electrode 16 and to the pulse voltage source 21 which feeds a pulse voltage to the same discharge electrode 16 so that the control parameter values may be reduced to zero or to a value less than a predetermined fixed value close to zero, and automatic control is effected so as to provide the optimum values of operating parameters, that is, the largest main electric field intensity and the largest negative ionic current densities $i_-$ within the range where occurrence of back ionization is suppressed, by controlling the D.C. voltage $V_{dc}$ and the crest value $V_P$, pulse duration $\tau_p$ and pulse repetition frequency $f_p$ of the pulse voltage.

Besides, the novel bipolar ionic current probe unit according to the present invention can be used for automatic control of every type of electric dust-collecting apparatuses (for instance, a tri-electrode type electric dust-collecting apparatus provided with a third electrode in addition to a discharge electrode and a dust-collecting electrode) and for control of powder painting systems or electrostatic separator systems.

What is claimed is:

1. A bipolar ionic current probe unit comprising:
a tri-electrode probe, which includes
a narrow elongated central electrode insulatively disposed on an imaginary surface of a small shape having a plane of symmetry along a line of intersection between said imaginary surface and said plane of symmetry, and
a pair of measuring electrodes insulatively disposed on said imaginary surface portions on the opposite sides of said central electrode in a symmetric manner with respect to said line of intersection so as to cover substantially the entire imaginary surface portions on the opposite sides with a small fixed gap clearance spaced from said central electrode;
a hollow metallic support post for insulatively supporting said tri-electrode probe; and
a measuring system which includes
individual electric conductors respectively connected to said said central electrode and said measuring electrodes and extending through the hollow space in said hollow metallic support post as insulated from said hollow metallic support post and from each other,
means for measuring minute electric currents with one end connected to said individual electric conductors and the other end connected through a common electric conductor to said hollow metallic support post, and
a variable D.C. voltage source connected between said common electric conductor and a reference potential point.

2. A method for simultaneously and individually measuring positive and negative ionic current densities within an electric field where both positive and negative ions coexist by mean of a bipolar ionic current probe unit comprising a tri-electrode probe, which includes a narrow elongated central electrode insulatively disposed on an imaginary surface of a small shape having a plane of symmetry along a line of intersection between said imaginary surface and said plane of symmetry and a pair of measuring electrodes insulatively disposed on said imaginary surface portions on the opposite sides of said central electrode in a symmetric manner with respect to said line of intersection so as to cover substantially the entire imaginary surface portions on the opposite sides with a small fixed gap clearance spaced from said central electrode, a hollow metallic support post for insulatively supporting said tri-electrode probe, and a measuring system, which includes individual electric conductors respectively connected to said central electrode and said measuring electrodes and extending through the hollow space in said hollow metallic support post as insulated from the hollow metallic support post and from each other, means for measuring minute electric currents with one end connected to said individual electric conductors and the other end connected through a common electric conductor to said hollow metallic support post, and a variable D.C. voltage source connected between said common electric conductor and a reference potential point; consisting of the steps of:
positioning said tri-electrode probe at a measuring point within said electric field as oriented in such direction that said plane of symmetry is directed in perpendicular to the direction of said electric field with one of said measuring electrode opposed to a source of negative ions and the other measuring electrode opposed to a source of positive ions;
varying the voltage of said variable D.C. voltage source to change the potentials of the central electrode and the measuring electrodes in said tri-electrode probe as well as said hollow metallic support post until said minute electric current measuring means detects substantially zero current flowing through the individual electric conductor connected to said central electrode;
then measuring the minute electric currents flowing through the individual electric conductors connected to said respective measuring electrodes; and
deriving the positive and negative ionic current densities, respectively, on the basis of the measured values of said minute electric currents flowing through the individual electric conductors connected to said respective measuring electrodes.

3. An automatic control system for an electric dust-collecting apparatus characterized in that the bipolar ionic current probe unit as claimed in claim 1 is used as means for detecting a back ionization current in said electric dust-collecting apparatus, and an output of a power supply for applying a voltage to said electric dust-collecting apparatus is automatically controlled according to the detected back ionization current.

4. A bipolar ionic current probe unit as claimed in claim 1, characterized in that said tri-electrode probe is disposed within an electric field in a dust-collecting space formed between a discharge electrode and a dust-collecting electrode in a dust-collecting apparatus as oriented in such direction that said plane of symmetry is directed in perpendicular to the direction of said electric field with one of said measuring electrode opposed to said discharge electrode and the other measuring electrode opposed to said dust-collecting electrode.

* * * * *